US00PP17168P3

(12) United States Plant Patent
Drewlow

(10) Patent No.: US PP17,168 P3
(45) Date of Patent: Oct. 24, 2006

(54) ***KALANCHOE* PLANT NAMED 'FOREVER MAXI NEON ROSE'**

(50) Latin Name: *Kalanchoe blossfeldiana*
Varietal Denomination: Forever Maxi Neon Rose

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/210,242

(22) Filed: Aug. 23, 2005

(65) Prior Publication Data

US 2006/0041971 P1 Feb. 23, 2006

Related U.S. Application Data

(60) Provisional application No. 60/603,806, filed on Aug. 23, 2004.

(51) Int. Cl.
*A01H 5/00* (2006.01)

(52) U.S. Cl. ..... Plt./339

(58) Field of Classification Search ..... Plt./339
See application file for complete search history.

*Primary Examiner*—Kent Bell
*Assistant Examiner*—June Hwu
(74) *Attorney, Agent, or Firm*—The Webb Law Firm

(57) ABSTRACT

A new and distinct cultivar of *Kalanchoe* plant name 'Forever Maxi Neon Rose', characterized by upright, dense and uniform plant habit; freely branching growth habit; numerous dark cherry rose-colored flowers; and excellent post-production longevity.

1 Drawing Sheet

Botanical classification: *Kalanchoe blossfeldiana.*
Varietal denomination: 'Forever Maxi Neon Rose'.

BACKGROUND OF INVENTION

The present invention comprises a new and distinct cultivar of *Kalanchoe blossfeldiana*, and hereinafter referred to by the varietal name 'Forever Maxi Neon Rose'. The new variety is a product of a planned breeding program conducted in Lompoc, Calif. The purpose of the breeding program was to create earlier flowering cultivars with large flower size and full flower clusters over the top of the plant. The new variety was selected from a seedling population which originated from a cross-pollination of a proprietary selection of *Kalanchoe blossfeldiana* identified as code number 98-109-2, not patented, as the female seed parent with a proprietary selection of *Kalanchoe blossfeldiana* identified as code number 96-182-2, not patented, as the male pollen parent. Comparisons between the new variety and its parents cannot be made, as the parental varieties no longer exist. The cultivar 'Forever Maxi Neon Rose' was discovered and selected in a controlled environment in Lompoc, Calif. Asexual reproduction of the new variety by terminal vegetative cuttings has shown that the unique features of this new variety are stable and reproduced true to type in successive propogations.

The following traits have been repeatedly observed and are determined to be the unique characteristics of 'Forever Maxi Neon Rose'. Characteristics that distinguish 'Forever Maxi Neon Rose' as a new and distinct cultivar from others known to the breeder include:

1) Medium height;
2) Good lateral and basal branching;
3) No heat delay with night temperatures of 22° C.;
4) Flower color of 53C to 57B;

5) Large flower size of 20 mm;
6) Excellent post-production longevity; and
7) Early to flower, flowering 9 to 9.5 weeks after start of short day treatment.

Plants of the new variety can be compared to plants of the *Kalanchoe* cultivar 'Forever Maxi Orchid', disclosed in U.S. Plant Pat. No. 12,413. In side-by-side comparisons conducted in Lompoc, Calif., plants of the new variety differed from plants of the cultivar 'Forever Maxi Orchid' in the following characteristics:

1) Flower color of the new variety was 53C to 57B, whereas the flower color of 'Forever Maxi Orchid' was 63B;
2) Flower size of the new variety was 20 mm, whereas the flower size of 'Forever Maxi Orchid' was 18 mm;
3) Time to flower in the summer from the start of short day treatment for the new variety was 9 to 9.5 weeks, whereas the time to flower for 'Forever Maxi Orchid' was 9.5 to 10 weeks;
4) Leaf color of the new variety was 147A, whereas the leaf color of 'Forever Maxi Orchid' was 147A with a reddish cast to the leaf edges of 181A; and
5) Leaf shape of the new variety is ovate with crenate margins and large shallow lobes, whereas the leaf shape of 'Forever Maxi Orchid' is oval with almost dentate margins that are shallow lobed.

BRIEF DESCRIPTION OF THE DRAWING

The accompanying colored photographic drawing illustrates the new variety, with the colors being as nearly true as is possible to obtain in colored illustrations of this type.

DESCRIPTION OF THE PLANT

Figure 1:
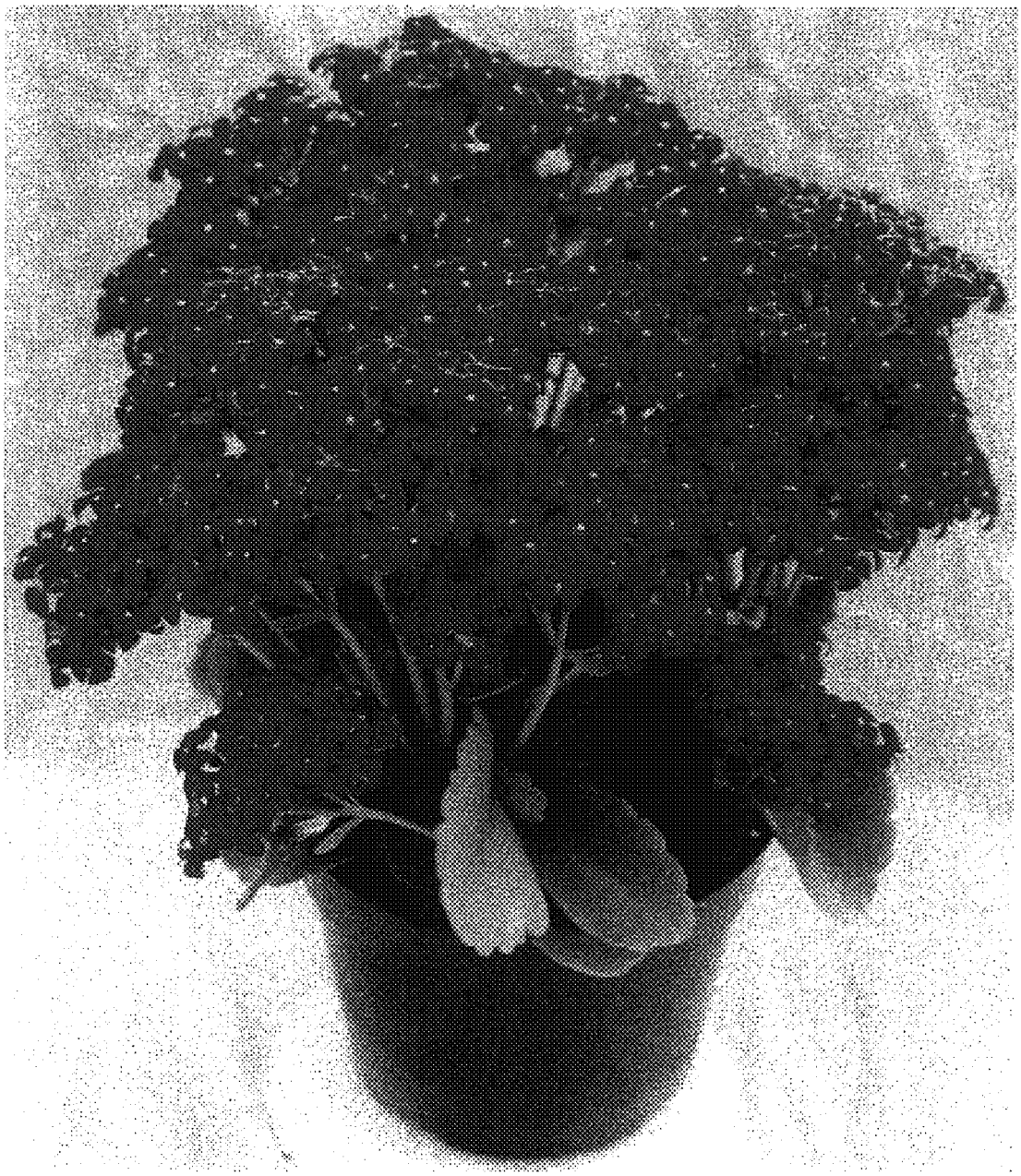

The cultivar 'Forever Maxi Neon Rose' has not been observed under all possible environmental conditions. The phenotype may vary somewhat with variations in environment such as temperature, day length and light intensity. However, there is no variance in genotype.

In the following description, color references are made to The Royal Horticultural Society Colour Chart, 1995 Edition, except where general terms of ordinary dictionary significance are used. Plants were grown during the late winter through early spring of 2003 in Lompoc, Calif., in a corrugated polycarbonate-covered greenhouse with 30% shade covering. During the production of the plants, day temperatures ranged from 20 to 22° C.; night temperatures ranged from 16 to 18° C. and light levels averaged 4000 foot candles of light. Rooted cuttings were planted in 15 cm containers and received long day/short night conditions (more than 14 hours of light) for about three weeks; plants then received natural short day/long night conditions (minimum 14 hours darkness) until flowering. Plants were about 11 weeks from the start of the short day/long night treatment when the photographs and the description were taken.

Propagation:

*Type cutting.*—Terminal vegetative cuttings.

*Time to initiate roots.*—Summer: About 10 days at 21° C. Winter: About 12 days at 21° C.

*Time to produce a rooted cutting.*—Summer: About 21 days at 21° C. Winter: About 21 days at 21° C.

*Root description.*—Fine fibrous, freely branching, moderately dense and grayed white in color.

Plant description:

*Form.*—Upright, uniform and dense plant habit. Freely flowering with numerous compound cymes. Inverted triangle; mounded crown. Appropriate for 10 to 15 cm containers; vigorous growth habit.

*Plant height at flowering.*—18 to 20 cm.

*Plant diameter at flowering.*—20 to 22 cm.

*Branching habit.*—Freely branching habit; typically 10 to 12 lateral branches develop per plant. Pinching (removal of terminal apex) is not required but will enhance lateral branch development.

*Lateral branch description.*—Length: About 8 to 16 cm. Diameter: About 3 to 4 mm. Internode length: About 1 to 1.5 cm. Aspect: About 35 to 40° from vertical. Strength: Very strong. Texture: Smooth, glabrous. Color: 146C.

*Foliage description.*—Arrangement: Opposite, simple. Length: About 7 to 8 cm. Width: About 6 to 7 cm. Shape: Ovate. Apex: Obtuse. Base: Acute to rounded. Margin: Crenate, large shallow lobes. Texture, upper and lower surfaces: Coriaceous, glabrous, and succulent. Venation pattern: Pinnate. Color: Developing leaves, upper surface: 146B. Developing leaves, lower surface: 146C. Fully expanded leaves, upper surface: 147A. Fully expanded leaves, lower surface: 147B. Venation, upper surface: 147A. Venation, lower surface: 147B. Petiole length: About 12 mm. Petiole diameter: About 5 mm. Petiole texture: Smooth, glabrous. Petiole color, upper surface: 147A. Petiole color, lower surface: 146A.

Flower description:

*Flower type and habit.*—Single flowers arranged in axillary compound dichasial cymes. Freely flowering; more than 30 flowers per lateral branch and more than 250 flowers per plant. Flowers not persistent. Flowers not fragrant. Flowers face mostly upright.

*Natural flowering season.*—Plants of the new *Kalanchoe* initiate and develop flowers under short day/long night conditions or during the late autumn/winter/early spring. Flower initiation and development can also be induced under artificial short day/long night conditions (at least 14 hours of darkness).

*Time to flower.*—Under short day/long night photoinductive conditions, about 9.0 to 9.5 weeks are required. Actual time to flower is primarily dependent upon temperature and light intensity.

*Post-production longevity.*—Excellent post-production longevity; plants maintain good foliage and flower substance for at least four weeks under interior environmental conditions.

*Flower diameter.*—About 2 cm.

*Flower height.*—About 1 cm.

*Flower buds.*—Shape: Oblong. Length: About 1.4 cm. Width: About 4 mm. Color: 146C, towards apex, 61B.

*Petals.*—Quantity: Four fused at base. Length: About 9 mm. Width: About 8 mm. Shape: Ovate to rounded. Apex: Cuspidate. Margin: Entire. Texture, upper and lower surfaces: Glabrous, smooth, soft. Color: When opening, upper surface: 53C. When opening, lower surface: 55B. Fully opened, upper surface: 53C to 57B, fading to 67A. Fully opened, lower surface: 64C.

*Sepals.*—Quantity: Four fused at base. Length: About 6 mm. Width: About 4 mm. Shape: Lanceolate. Apex: Acuminate. Base: Rounded. Margin: Entire. Texture, upper and lower surfaces: Glabrous, smooth. Color: Immature, upper surface: 146D. Immature, lower surface: 146D. Mature, upper surface: 146C. Mature, lower surface: 146C.

*Calyx.*—Shape: Cupped. Length: About 10 mm. Diameter: About 4 mm.

*Peduncles.*—Length: About 2 cm. Diameter: About 4 mm. Angle: About 45° from vertical. Strength: Strong. Texture: Smooth, glabrous. Color: 146C.

*Pedicels.*—Length: About 3 mm. Diameter: About 1 mm. Angle: About 45°. Texture: Smooth, glabrous. Color: 146B.

*Reproductive organs.*—Stamens: Quantity per flower: Eight. Anther shape: Elliptic, flat. Anther size: Less than 1 mm. Anther color: Yellowish green. Pollen amount: Abundant. Pollen color: Yellow. Pistils: Quantity per flower: Four. Style length: About 4 mm. Style color: 146D. Stigma shape: Flat. Stigma color: White. Ovary color: 146C.

*Seed.*—Quantity per ovary: More than 100. Length: Less than 1 mm. Diameter: Less than 1 mm.

Disease/pest resistance: Plants of the new variety have not been observed to date to be resistant to pathogens and pests common to *Kalanchoes*.

Temperature tolerance: Plants of the new variety have been observed to tolerate low temperatures of 10° C. and high temperatures of 35° C.

I claim:

1. A new and distinct variety of *Kalanchoe* plant named 'Forever Maxi Neon Rose' as herein described and illustrated.

* * * * *